US011422127B2

(12) United States Patent
Gosselin et al.

(10) Patent No.: US 11,422,127 B2
(45) Date of Patent: Aug. 23, 2022

(54) EX VIVO ANTIGEN AND ADJUVANT PULSED PERIPHERAL BLOOD MONONUCLEAR CELLS AS A SCREENING PLATFORM FOR CANDIDATE NOVEL VACCINES AND CANDIDATE ANTIGENS

(71) Applicant: ALBANY MEDICAL COLLEGE, Albany, NY (US)

(72) Inventors: Edmund J. Gosselin, Glenmont, NY (US); Sudeep Kumar, Albany, NY (US); David Nalin, West Chester, PA (US)

(73) Assignee: ALBANY MEDICAL COLLEGE, Albany, NY (US)

( * ) Notice: Subject to any disclaimer, the term of this patent is extended or adjusted under 35 U.S.C. 154(b) by 102 days.

(21) Appl. No.: 16/463,704

(22) PCT Filed: Dec. 7, 2017

(86) PCT No.: PCT/US2017/064989
§ 371 (c)(1),
(2) Date: May 23, 2019

(87) PCT Pub. No.: WO2018/106849
PCT Pub. Date: Jun. 14, 2018

(65) Prior Publication Data
US 2019/0376951 A1 Dec. 12, 2019

Related U.S. Application Data

(60) Provisional application No. 62/431,115, filed on Dec. 7, 2016.

(51) Int. Cl.
*A61K 39/09* (2006.01)
*G01N 33/50* (2006.01)
*A61P 31/04* (2006.01)
*A61K 9/00* (2006.01)
*A61K 39/02* (2006.01)
*A61K 39/39* (2006.01)
*C12N 5/078* (2010.01)
*A61K 39/00* (2006.01)

(52) U.S. Cl.
CPC ....... *G01N 33/5014* (2013.01); *A61K 9/0043* (2013.01); *A61K 39/0208* (2013.01); *A61K 39/092* (2013.01); *A61K 39/39* (2013.01); *A61P 31/04* (2018.01); *C12N 5/0634* (2013.01); *A61K 2039/5158* (2013.01); *A61K 2039/543* (2013.01); *C12N 2500/72* (2013.01); *C12N 2503/02* (2013.01)

(58) Field of Classification Search
None
See application file for complete search history.

(56) References Cited

U.S. PATENT DOCUMENTS

| 5,723,127 A | 3/1998 | Scott et al. |
| 7,405,077 B2 | 7/2008 | Lim et al. |
| 2010/0215674 A1* | 8/2010 | Thielemans ............ A61P 31/12 424/184.1 |

FOREIGN PATENT DOCUMENTS

CA 2974237 A1 7/2016

OTHER PUBLICATIONS

Iglesias et al. Immunology and Cell Biology 18, Oct. 2012, vol. 91, issue 2, pp. 139-148 (Year: 2012).*
Biksaktsis et al. Infection and Immunity vol. 80, No. 3 pp. 1166-1180, 2011. (Year: 2011).*
Li Pira et al. Clinical and Vaccine Immunology, vol. 15, No. 12, pp. 1811-1818, Dec. 2008 (Year: 2008).*
Iglesias et al. "Multiple Mechanisms Mediate Enhanced Immunity Generated by mAb-Inactivated F. tularensis Immunogen," Immunology & Cell Biology, Dec. 18, 2012 (Dec. 18, 2012), vol. 91, Iss. 2, pp. 139-148. entire document.
Biksaktsis et al. "Mucosal Immunization with an Unadjuvanted Vaccine That Targets *Streptococcus pneumoniae* PspA to Human Fcγ Receptor Type I Protects against Pneumococcal Infection through Complement- and Lactoferrin-Mediated Bactericidal Activity," Infection and Immunity, Dec. 12, 2011 (Dec. 12, 2011), vol. 80, No. 3, pp. 1166-1180. entire document.
Datta et al. "Rationale for a Multimodality Strategy to Enhance the Efficacy of Dendritic Cell-Based Cancer Immunotherapy," Fontiers in Immunology, Jun. 2, 2015 (Jun. 2, 2015), vol. 6, Article 2/1, pp. 1-11. entire document.
Anderson et al. "Long Lived Protection against Pneumonic Tularemia is Correlated with Cellular Immunity in Peripheral, Not Pulmonary, Organs," Vaccine, Aug. 3, 2010 (Aug. 3, 2010), vol. 28, No. 40, pp. 6562-6572. entire document.

(Continued)

*Primary Examiner* — Jana A Hines
*Assistant Examiner* — Khatol S Shahnan Shah
(74) *Attorney, Agent, or Firm* — Bond Schoeneck and King PLLC; David Nocilly

(57) ABSTRACT

Peripheral blood mononuclear cells (PBMCs) can be used in place of DCs when pulsing with antigens, or antigen and adjuvant combination, and then administered to a subject as a vaccine to induce a protective immune response. The PBMC-based vaccine strategy provides a more marked and enduring protective immune response and is also capable of serving as a multi-organism prophylactic vaccine platform. The vaccine platform may be used to screen vaccine and adjuvant combinations and may also be used to allow for adjuvants that are otherwise unsafe for use in humans as the adjuvant may be removed prior to prophylactic administration of the pulsed PBMCs.

4 Claims, 7 Drawing Sheets

(56) References Cited

OTHER PUBLICATIONS

Figure 1:
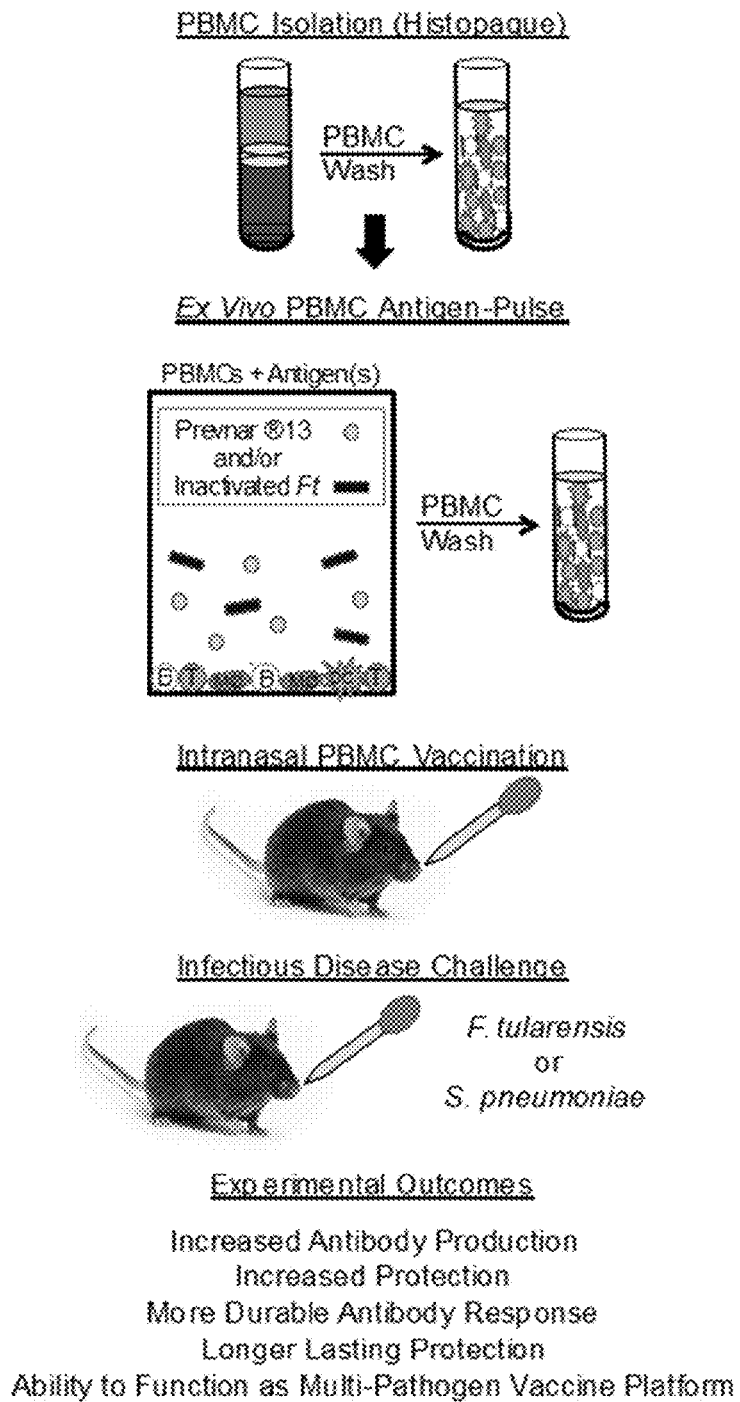

International Search Report and Written Opinion Form PCT/ISA/220 and PCT/ISA/237, International Application No. PCT/US2017/064989, pp. 1-10, International Filing Date Dec. 7, 2017, dated Mar. 20, 2018.

* cited by examiner

EX VIVO ANTIGEN AND ADJUVANT PULSED PERIPHERAL BLOOD MONONUCLEAR CELLS AS A SCREENING PLATFORM FOR CANDIDATE NOVEL VACCINES AND CANDIDATE ANTIGENS

STATEMENT REGARDING FEDERALLY SPONSORED RESEARCH OR DEVELOPMENT

This invention was made with government support under Grant No. NIH R01 A100138 awarded by the National Institutes of Health (NIH). The government has certain rights in the invention.

BACKGROUND OF THE INVENTION

1. Field of the Invention

The present invention relates to enhanced immunity and, more specifically, to the use of vaccine and adjuvant pulsed peripheral blood mononuclear cells for a protective immune response, as a multi-organism vaccine platform, and also as a screening platform for candidate novel vaccines and candidate adjuvants.

2. Description of the Related Art

Dendritic cells (DCs) are the most efficient antigen (Ag) presenting cells (APCs) at taking up, processing, and presenting Ags to naïve T cells. This property of DCs has been harnessed to develop DC-based immunotherapeutics and therapeutic vaccines against cancer and a number of infectious diseases, including HIV-1 and influenza. Typically, use of DC-based immunotherapeutics and vaccines involve a number of ex vivo manipulations, including isolation of DCs or DC precursors followed by in vitro differentiation into DCs and, in some cases, induction of DC maturation. The DCs are then mixed ex vivo with vaccine Ags in the presence or absence of DC maturation factors for 3-7 days and subsequently administered back into the vaccine recipient. Importantly, the process of DC isolation/differentiation is cumbersome, requires a high level of skill, time, and infrastructure, and is expensive. Thus, such a treatment can be difficult to utilize in the clinic, in particular in underdeveloped countries.

In contrast, peripheral blood mononuclear cells (PBMCs) contain numerous APC populations including: monocytes/macrophages, DCs, and B cells, all of which are fully capable of processing and presenting vaccine Ags to T cells and thereby stimulating an immune response. In addition, PBMCs are more easily and rapidly isolated, requiring minimal infrastructure and expense. However, successful studies utilizing PBMCs in place of DCs in an ex-vivo vaccine platform are rare. Specifically, in one case PBMCs were successfully used as a treatment to deliver vaccine Ags, which was shown to ameliorate prostate cancer. As a result of these studies, this vaccine has now been approved by the FDA as an immunotherapeutic for castration-resistant prostate cancer. In contrast to therapeutic applications, there has been no application of a PBMC platform to prophylactic use, either of vaccines to prevent disease by immunization or to screen the efficacy of vaccines or of adjuvants for such prophylactic vaccines.

Numerous studies have demonstrated that administration of antigen (Ag)-pulsed dendritic cells (DCs) is an effective strategy for enhancing immunity to tumors and infectious disease organisms. However, the generation and/or isolation of DCs can require substantial time and expense. Accordingly, there is a need in the art for a simpler, less time consuming, and less expensive approach to DC-based vaccines and vaccination in general.

BRIEF SUMMARY OF THE INVENTION

The present invention comprises the use of a use of PBMC platform for screening of candidate prophylactic vaccines and candidate prophylactic adjuvants for immunogenicity and safety. Using inactivated *F. tularensis* (iFt) Ag as a model immunogen, it was determined that DCs could be replaced with peripheral blood mononuclear cells (PBMCs) during the ex-vivo pulse phase and still provide protection against Ft infection. Follow up studies were then conducted using the *S. pneumoniae* (Sp) vaccine Prevnar®13 as the Ag in the pulse phase followed by immunization and Sp challenge. In both cases, it was demonstrated that PBMCs can be used in place of DCs when pulsing with iFt and/or Prevnar®13 ex vivo and re-administering the Ag-pulsed PBMCs as a prophylactic vaccine. In addition, utilization of the i.n. route for Ag-pulsed PBMC administration is superior to use of the i.v. route in the case of Sp immunization, as well as when compared to direct injection of Prevnar®13 vaccine i.m. or i.n. Furthermore, this PBMC-based vaccine strategy provides a more marked and enduring protective immune response and is also capable of serving as a multi-organism vaccine platform. This ex-vivo vaccine strategy provides a simpler, less time consuming, less traumatic, and less expensive approach to DC-based vaccines and vaccination in general and makes feasible use of the PBMC platform for prophylactic vaccination and for screening for effective prophylactic vaccines and adjuvants.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a schematic of an approach using Ag-pulsed peripheral blood mononuclear cells (PBMCs) according to the present invention.

FIGS. 2(A) through (C) are a series of graphs showing that iFt-pulsed PBMCs generate protection against lethal Ft LVS challenge and Ft LVS specific Abs: Freshly isolated PBMCs were pulsed with iFt at a ratio of 100 organisms/cell. Mice were administered (i.v.) two doses (two weeks apart) of 50 μl of PBS, $5\times10^5$ PBMCs alone, or $5\times10^5$ iFt-pulsed PBMCs. (A) Two weeks post-boost mice were infected with $1\times10^4$ CFU of Ft (i.n.) and their survival was monitored for 21 days. Values represent two independent experiments (n=12). (B and C) Two weeks post-boost, serum was collected and analyzed for Ft-specific IgG (B) and IgA (C) via ELISA. Values represent the mean±SEM (n=12) from two independent experiments. Significantly different groups (compared to PBS) are indicated with *($p<0.05$) or **** ($p<0.0001$).

FIGS. 3(A) through (B) are a series of graphs showing that Prevnar®13-pulsed PBMCs generate protection against lethal Sp challenge and Sp specific Ab. PBMCs were pulsed with immunogen as described in FIG. 1 with slight modifications. Specifically, in this experiment, PBMCs were pulsed with 9.34 μg/ml Prevnar®13. Mice were then administered i.v. two doses (two weeks apart) of 50 μl PBS, $5\times10^5$ PBMCs alone, or $5\times10^5$ Prevnar®13-pulsed PBMCs. Positive controls included mice directly injected i.v. or i.m. with 1.7 µg of Prevnar®13 alone. (A) Four weeks post-boost, mice were infected (i.n.) with $2 \times 10^6$ CFU of type 3 Sp and their survival was subsequently monitored for 21 days. Values represent one experiment (n=6). (B) Twenty-five days post-boost, serum was collected and analyzed for total Sp-specific Ab via ELISA. Values represent the mean±SEM (n=6). Significantly different groups (compared to PBS) are indicated with ***($p<0.001$) or *($p<0.05$).

Figure 4:
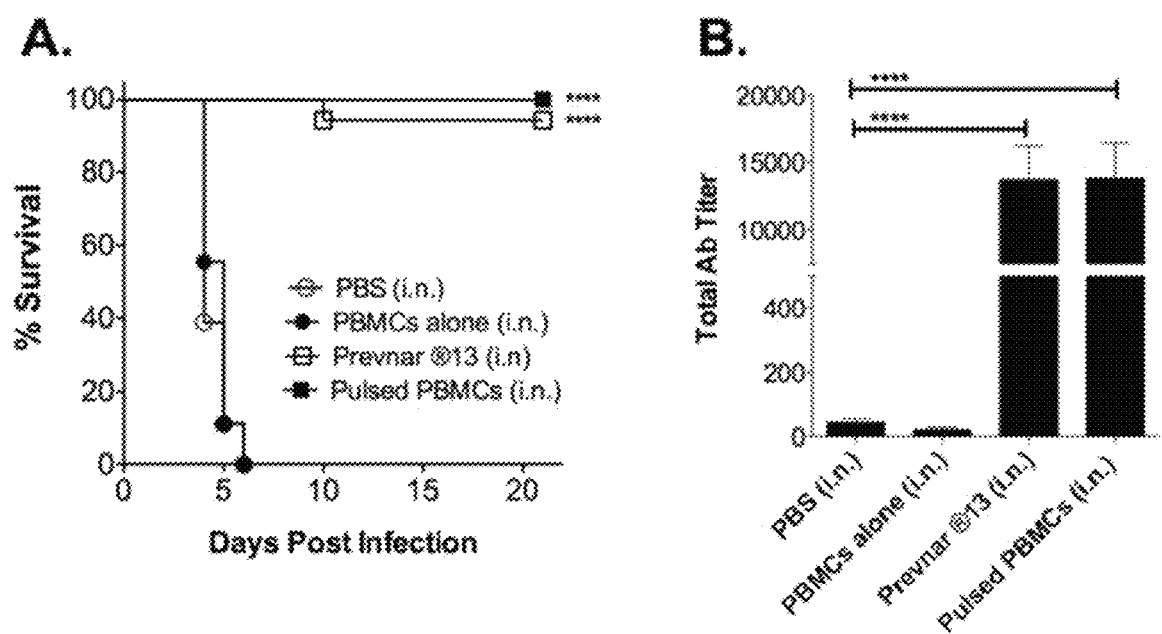

FIGS. 4(A) through (B) are a series of graphs showing that Prevnar®13-pulsed PBMCs administered i.n. also generate protection and Sp specific Ab. PBMCs were pulsed with 18.68 µg/ml Prevnar®13. Mice were then administered i.n. 28 µl of PBS or in 28 µl PBS; $5 \times 10^5$ PBMCs alone, or $5 \times 10^5$ Prevnar®13-pulsed PBMCs. Mice in the positive control group received 1.7 µg of Prevnar®13 alone. (A) Four weeks post-boost, mice were infected with $2 \times 10^6$ CFU of type 3 Sp and their survival was subsequently monitored for 21 days. Values represent three independent experiments (n=18). Significantly different groups (compared to PBS) are indicated with *($p<0.001$). (B) Twenty-five days post-boost, serum was collected and analyzed for total Sp-specific Ab via ELISA. Values represent three independent experiments (n=18). Data were analyzed by Mann-Whitney U test. Significantly different groups (compared to PBS) are indicated with ($p<0.05$).

Figure 5:
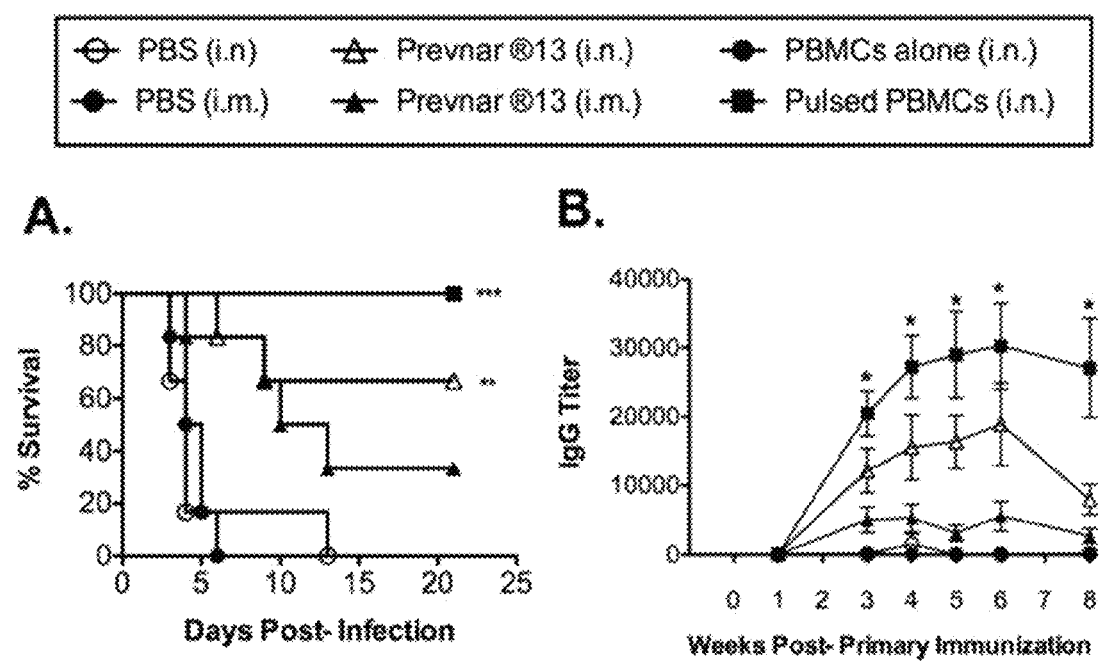

FIGS. 5(A) through (B) are a series of graphs showing that Prevnar®13-pulsed PBMCs administered i.n. induce a more marked, stronger, and longer-lived Sp-specific Ab response, as well as enhanced survival. PBMCs were pulsed with 18.68 µg/ml Prevnar®13. Mice were immunized on days 0 and 14 (red font) i.n. or i.m. with PBS, PBMCs only, Prevnar®13 alone, or Prevnar®13-pulsed PBMCs (A) Mice were challenged on week 14 with $2 \times 10^6$ CFU of Sp (serotype 3, strain A66.1). The values presented represent those from one of two similar experiments with similar results (n=6). Significantly different groups (compared to PBS) are indicated with ***($p<0.001$) or *($p<0.01$). (B) Sp-specific serum IgG titers were measured at the time intervals indicated. A statistically significant difference was observed when comparing Ab titers from mice immunized with Prevnar®13-pulsed PBMCs administered i.n. versus direct administration of Prevnar®13 alone i.n. The values presented represent those from one of two similar experiments with similar results (n=6). Significantly different groups (compared to PBS) are indicated with *($p<0.05$).

FIGS. 6(A) through (F) are a series of graphs showing that the Ag-pulsed PBMC vaccine strategy can also serve as a multi-organism vaccine platform. Mice were immunized with PBS (A, B, C, D, E and F), PBMCs alone (A, B, C, D, E and F), PBMCs pulsed with iFt alone (A, C, and E), PBMCs pulsed with Prevnar®13 alone (B, D, and F), PBMCs pulsed with iFt and Prevnar®13 separately and mixed before immunization (A and B) or PBMCs pulsed simultaneously with iFt and Prevnar®13 (C, D, E, and F). Four weeks post-boost mice were challenged with either 2100 CFU of Ft (A and C) or $2 \times 10^6$ CFU of Sp (B and D). Survival was monitored for 21 days. Values represent one experiment (n=6 mice/group for PBS and PBMC groups and 8 mice/group for Ag-pulsed PBMCs groups). Significantly different groups (compared to PBS) are indicated with *($p<0.05$) **($p<0.0001$), *($p<0.001$) or *($p<0.05$). (E and F) Three weeks post-boost, sera was obtained from all the groups and analyzed for Ft-specific IgG (C) or Sp-specific IgG (D). Values represent the mean±SEM (n=12) from two independent experiments. Significantly different groups (compared to PBS) are indicated with *($p<0.05$) or ****($p<0.01$).

FIGS. 7(A) through (C) are a series of graphs showing the results of freshly isolated PBMCs that remained unstimulated or were pulsed with iFt, Prevnar®13, or both and then stained for expression of activation markers with the following monoclonal antibodies: anti-CD11b-Alexa fluor 488, anti-CD19-PE, anti-CD40-APC, anti-CD86-Alexa fluor 700, or anti-CD197-PE-Cy7 BD.

DETAILED DESCRIPTION OF THE INVENTION

Referring to the figures, wherein like numerals refer to like parts throughout, there is seen in FIG. 1 an approach using Ag-pulsed peripheral blood mononuclear cells (PBMCs) for an improved protective immune response and as a multi-organism vaccine platform according to the present invention. To confirm the present invention, DCs were replaced with PBMCs that were pulsed ex vivo with inactivated *F. tularensis* LVS (iFt) and/or the *S. pneumoniae* (Sp) vaccine Prevnar®13. Ft LVS is an attenuated form of the human virulent Ft, which is a category A biothreat agent. Importantly, antibody (Ab) is the primary mediator of protection against Sp and can also play a primary role in the protection of mice against Ft LVS challenge. Thus, the testing focused on humoral immunity and the ability of Ag-pulsed PBMCs to generate a protective humoral immune response to Ft LVS and Sp. PBMCs pulsed with iFt and/or Prevnar®13 ex vivo generated both Ag-specific Ab responses and subsequent protection against both Ft and Sp either as individual vaccines or when combined as a multi-organism vaccine. In addition, the intranasal (i.n.) route of Ag-pulsed PBMC vaccine delivery was found to be superior to the intravenous (i.v.) route in the case of Sp immunization and challenge, as well as when compared to the direct injection of Prevnar®13 intramuscularly (i.m.) or i.n. Furthermore, the PBMC-based vaccine strategy of the present invention provides a more marked and enduring protective immune response. The PBMC vaccination platform of the present invention may be used with any other antigen or antigen and adjuvant combination, including those not fit for in vivo use in humans, following the experimental protocol explained below, such as influenza, human immunodeficiency virus (HIV), as well as with both single vs multiple simultaneous vaccines and vaccine candidates.

EXAMPLE 6-8 week old inbred female C57BL/6 mice were purchased from Taconic Laboratories (Hudson, N.Y.) and housed in Animal Resource Facility of Albany Medical College. The animal studies were reviewed and approved by the Institutional Animal Care and Use Committee at Albany Medical College utilizing NIH standards.

PBMCs were isolated from freshly obtained whole blood from genetically identical C57Bl6 mice using density gradient separation [Histopaque 1083 (Sigma-Aldrich, St. Louis, Mo.)], following the manufacturer's instructions. Typically, 200-300 □l of blood were obtained from each mouse, with the blood yielding approximately $3-5 \times 10^6$ PBMCs/ml, which is sufficient for the immunization of one mouse. Thus, pooled blood (5-6 ml) from 20-30 mice was generally required to conduct an experiment. Blood was mixed with an equal volume of 2% fetal bovine serum (FBS) in phosphate buffered saline (PBS) at room temperature. Subsequently, blood was mixed with the anticoagulant sodium citrate at a 1:9 (sodium citrate: blood) ratio and maintained at room temperature to avoid cell clumping.

Next, 15 ml of Histopaque was poured into a 50 ml Sepmate tube (Vancouver, BC, Canada) and the pooled blood+FBS mixture gently layered onto the Histopaque. The tube was then centrifuged at 1200 g for 10 min at room temperature. The upper layer then was quickly transferred to a fresh 50 ml tube and centrifuged at 500 g for 5 minutes. Cell pellets were washed three times with PBS and finally re-suspended in 2 ml RPMI medium containing 10% FBS. Cell numbers were counted using a haemocytometer and adjusted as required. Importantly, the response of pooled cells would not be expected to differ if compared to the response of cells from a single animal, since inbred mice are being used as the source of blood. Specifically, even when mixed, the PBMCs from individual mice are genetically identical to and histocompatible with each other, as well as the mice into which they are being administered.

PBMCs ($4\times10^6$) were mixed with varying amounts of iFt Ag in 1 ml of RPMI 1640 medium supplemented with 10% FBS and then incubated for 3 h at 37° C. (5% $CO_2$). Subsequently, PBMCs were washed three times with 5 ml PBS. Finally, PBMCs were re-suspended in a sufficient volume of PBS to achieve the desired number of PBMCs/ml. The pulsed PBMCs were then used for immunization within 1 h after completion of Ag pulsing.

Groups of 6-8 female C57BL/6 mice were immunized on day 0 and 14 via the i.v., i.n., or i.m. route. Prior to administration, mice were anesthetized by intraperitoneal (i.p.) injection of 20% ketamine plus 5% xylazine before administering 28 µl (i.n.) or 50 µl (i.v.) of PBS (vehicle), Ag alone, PBMCs alone, Ag-pulsed PBMCs or challenge pathogens. Mice were then infected/challenged as described in each figure legend with Ft LVS or Sp serotype 3 (strain A66.1) via the i.n. route in 40 µl PBS and subsequently monitored for survival for at least 21 days.

Ab responses to immunization were measured by ELISA for anti-Ft Ab as previously reported and for anti-Sp Ab as follows. ELISA plates (Corning, Corning N.Y.) were coated with 50 µl of live Sp ($5\times10^7$ CFU/ml) or live Ft LVS in carbonate buffer [4.3 g/L sodium bicarbonate (Sigma-Aldrich)] and 5.3 g/L sodium carbonate (Sigma-Aldrich) (at pH 9.4) for 16 h at 4° C. Plates were then washed with washing buffer [PBS (Sigma) containing 0.5% BSA (Sigma)] and blocked for 2 hours with 200 µl of PBS containing 5% BSA. Serial 3-fold dilutions of sera (starting with 1:50) were added to the plates (50 µl/well) and incubated for 2 h at 4° C. After three washes with washing buffer, Alkaline-phosphatase-conjugated anti-mouse Abs specific for IgG or IgM (Sigma) were added to each well (50 µl/well). ELISA plates were then incubated for 1 hour at 4° C. and washed three more times with washing buffer. Next, 100 µl of BCIP/NBT (Alkaline-phosphatase substrate) (Sigma) was added and the plates were incubated for 1-3 h and optical density (OD) was read intermittently at 405 nm using a micro plate reader (Molecular Devices, Sunnyvale, Calif.). Using the Graph-Pad (Prizm) program, Ab titers were calculated as the EC50 (half maximal) value obtained by a 4-parameter non-linear regression curve between log reciprocal-dilution versus response (OD 405 nm).

The log-rank (Mantel-Cox) test was used for survival curves. For ELISA titers, 2-tailed Mann-Whitney U test was used to compare groups. Data analyses were performed using GraphPad Prism 5 (San Diego, Calif.).

Figure 2:
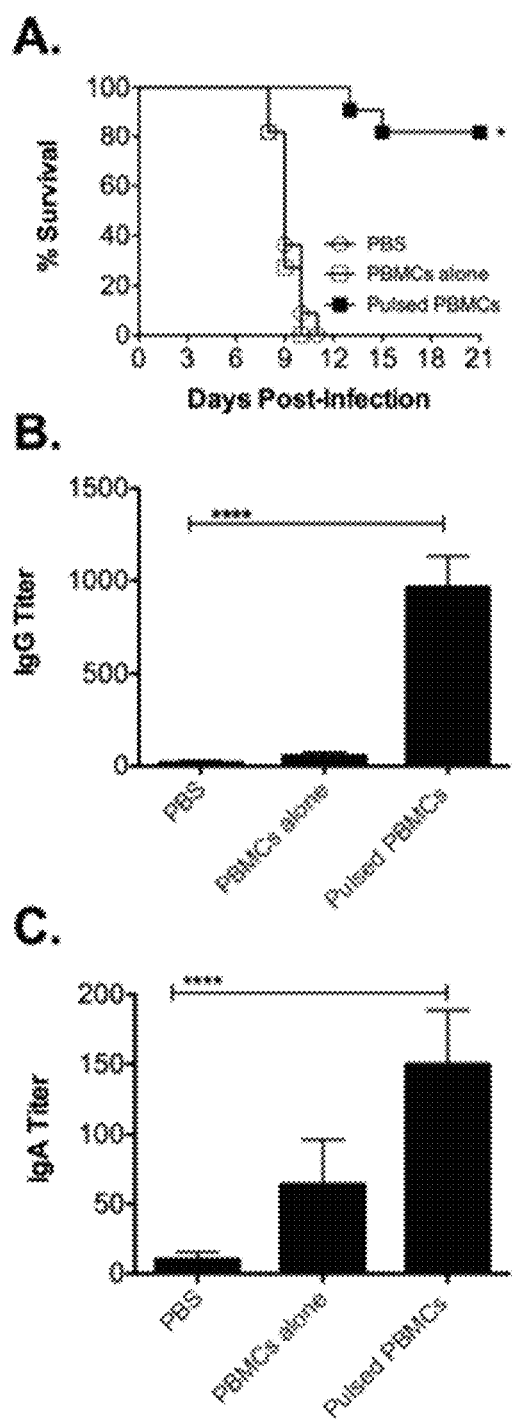

Intravenous administration of PBMCs pulsed ex vivo with iFt conferred protection against Ft challenge (FIG. 2A), which correlated with the increased production Ft-specific Ab. (FIGS. 2B and C). This is similar to our previous studies in which i.n. administration of iFt-pulsed DCs also protected against Ft challenge. However, while the number of iFt organisms/PBMC in this study was similar to that of iFt organisms/DC utilized in a previous study, one-third the number of PBMCs were needed to immunize as compared to DCs. It should however also be noted that the immunization route for this experiment (i.v.) [FIG. 2 (PBMCs)] differed from the immunization route of a previous study (i.n.) utilizing DCs. In regard to the focus on examining humoral immunity (Ab production), it should be noted that there is published data demonstrating that Ab can play a primary role in protection against Ft LVS infection, even at the lower titers observed in these studies. Lastly, it is also important to note that when immunizing with iFt-pulsed PBMCs administered i.v. and challenging with Ft LVS, bacteria were cleared in surviving mice (data not shown).

Figure 3:
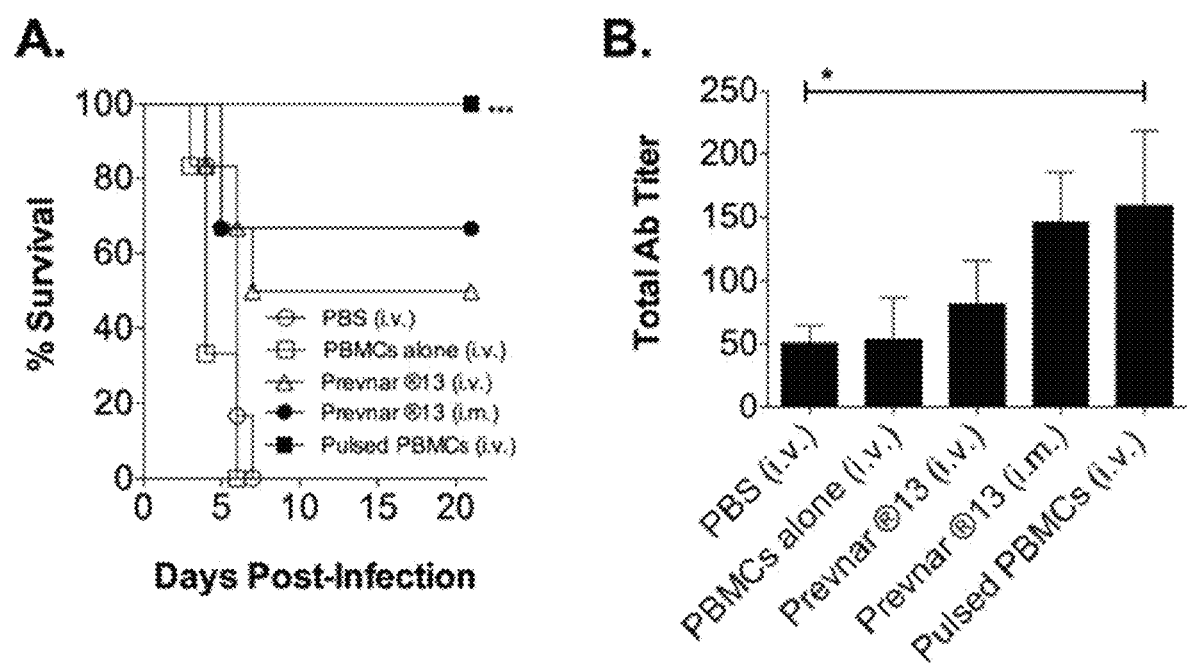

In order to further demonstrate the potential usefulness of this PBMC-based immunization strategy, a more well-defined and commonly used vaccine candidate was also utilized. In this case, the pneumococcal vaccine Prevnar®13 and an established mouse model was selected for evaluating vaccine efficacy against Sp. As demonstrated in FIG. 3A, 100% protection was observed when immunizing mice i.v. with Prevnar®13-pulsed PBMCs versus direct injection of Prevnar®13 i.v. or i.m. (50% and 63% protection, respectively). Furthermore, Prevnar®13 pulsed PBMCs induced a slight increase in Sp-specific Ab titers compared to Prevnar®13 administered alone (i.v.), while Prevnar®13 administered i.m. alone induced titers of Sp-specific Ab similar to that of Prevnar®13-pulsed PBMCs given i.m. (FIG. 3B). However, overall the Sp-specific Ab titers obtained following immunization were relatively low and the difference in survival between mice immunized with Prevnar®13 i.m. (63%) and Prevnar®13-pulsed PBMCs (100%) was not reflected in the Sp-specific Ab titers, suggesting that in this case and, as may also be the case in FIG. 2, the Ab titers examined may not be the sole determinant of survival.

The above studies focused on pulsed PBMCs given i.v., which is not a traditional route of human immunization. However, i.n. immunization offers a less invasive and potentially more desirable route of immunization. Thus, a study was performed to determine if the PBMC-based vaccine platform would be equally effective when administering Prevnar®13-pulsed PBMCs i.n. Importantly, when evaluating the i.v. route we tested the administration of 9.34, as well as 18.68 ug Prevnar®13, with the latter giving a slightly higher response (data not shown). Thus, the higher dose was used in subsequent i.n. immunization studies. As shown in FIG. 4A, survival results obtained were similar to those using the i.v. administration route, in that Prevnar®13-pulsed PBMCs administered i.n. induced 100% survival. Consistent with the latter, Prevnar®13-pulsed PBMCs also induced Sp-specific Abs (FIG. 4B). Notably, in this case, Sp-specific Ab titers induced by i.n. immunization were substantially higher than those obtained when using the i.v. route (FIG. 4B versus FIG. 3B, respectively).

The impact of PBMC-based vaccination on bacterial burden in the lungs of i.n. immunized mice was also investigated. Following immunization and challenge as described (FIG. 4), mice were euthanized at various time intervals and lung tissue was collected aseptically in PBS and subjected to mechanical homogenization using a Mini Bead Beater-8 (BioSpec Products, Bartlesville, Okla.) and 1-mm zirconia/silica beads. Tissue homogenates were then serially diluted 10-fold in sterile PBS. Subsequently, 10 µl of each dilution was spotted onto Trypticase Soy Agar with 5% Sheep Blood plates (BD biosciences, San Jose, Calif.) and incubated at 37° C. for 24 h. The number of colonies on the plates were then counted and expressed as total CFU per lung. As shown in Table 1 below, mice receiving PBS or PBMCs alone exhibited approximately a 2-3 log increase in bacterial burden on day 4 compared to day 2. In contrast, mice receiving the Prevnar®13 vaccine alone or Prevnar®13-pulsed PBMCs exhibited a 1-2 log reduction in bacterial burden on day 2 and a 3-5 log reduction in bacteria on day 4, when compared to mice immunized with PBS or PBMCs alone. On day 12 both the Prevnar®13 alone and Prevnar®13-pulsed PBMC groups had cleared the pathogen from their lungs, while those immunized with PBS or PBMCs alone had died.

Figure 6:
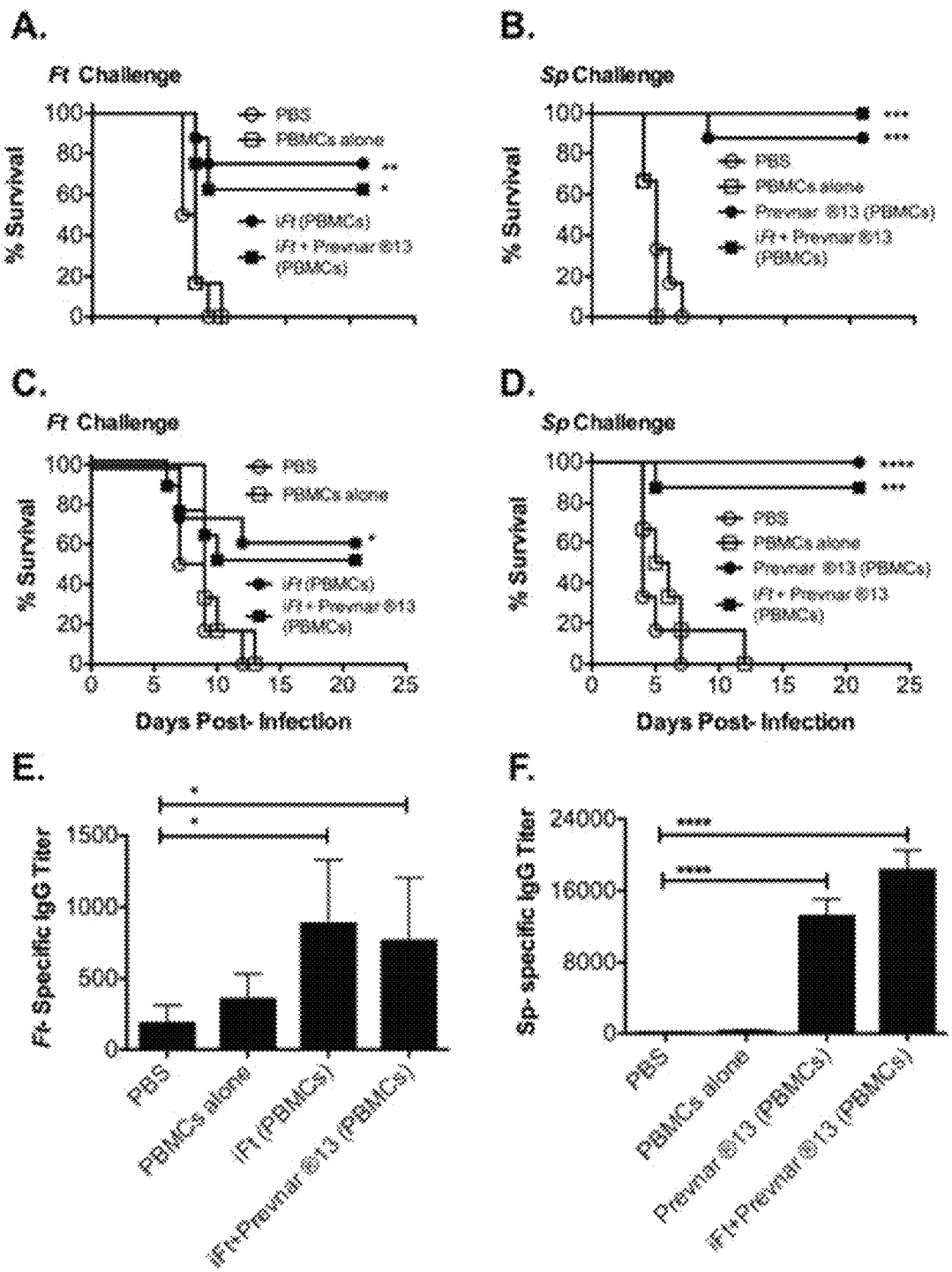

FIGS. 6A and 6B re-affirming that this PBMC-based vaccine approach can serve as a multi-organism vaccine platform. Also as observed when using the single pathogen PBMC-based vaccination protocols for Ft or Sp (FIGS. 2-5), both Ft-specific and Sp-specific Ab titers were increased substantially following immunization (FIGS. 6E and F).

PBMCs can thus efficiently deliver vaccine Ags and elicit immune protection against bacterial infection when pulsed ex vivo and re-administered as a vaccine either i.v. or i.n. Specifically, iFt or Prevnar®13-pulsed PBMCs induced protection against lethal challenge with Ft LVS or Sp, respectively. The protection also correlated with increased Ft LVS

TABLE 1

Evaluation of bacterial burden in the lungs of Prevnar ®13-pulsed PBMC- immunized mice

| Days post-infection | PBS | | PBMCs Alone | | Prevnar ®13 Alone | | Prevnar ®13-Pulsed PBMCs | |
|---|---|---|---|---|---|---|---|---|
| | Mean CFU* | S.E.M. | Mean CFU* | S.E.M. | Mean CFU* | S.E.M. | Mean CFU* | S.E.M. |
| Day 2 | $7.3 \times 10^5$ | $2.0 \times 10^5$ | $1.9 \times 10^6$ | $8.8 \times 10^5$ | $1.3 \times 10^4$ | $5.9 \times 10^4$ | $3.3 \times 10^3$ | $2.8 \times 10^3$ |
| Day 4 | $8.1 \times 10^7$ | $6.0 \times 10^7$ | $2.7 \times 10^8$ | $6.7 \times 10^7$ | $4.3 \times 10^3$ | $1.2 \times 10^3$ | $8.0 \times 10^4$ | $6.0 \times 10^4$ |
| Day 12 | ND** | | ND** | | None*** | | None*** | |

*Data represents total CFU per lung from one experiment (n = 3).
**ND: Not done (All the mice in these groups died before day 12).
***We did not observe any bacterial colonies in these tissues (lower detection limit was 100 colonies).

Prevnar®13-pulsed PBMCs administered i.n. induce a more marked, stronger, and longer-lived Sp-specific Ab response than Prevnar®13 administered alone, and enhanced survival. The strength and longevity of the response following i.n. administration of Prevnar®13-pulsed PBMCs versus i.m. or i.n. administration of Prevnar®13 vaccine alone was also determined. The Sp-specific Ab response following an i.n. boost with Prevnar®13-pulsed PBMCs was stronger, and longer-lived than that of i.n. administered Prevnar®13 vaccine (FIG. 5A) This difference was also greater compared to Prevnar®13 administered alone via the clinically approved i.m. route. Another similar experiment also generated similar Ab results (data not shown), as well as superior survival (FIG. 5B) following an Sp challenge 12 weeks post-boost.

Given the positive results using the PBMC-based vaccine strategy and Ft and Sp immunization and challenge models, we investigated whether the PBMC-based vaccine platform could induce protection against multiple pathogens simultaneously using iFt plus Prevnar®13-pulsed PBMCs administered i.n. Due to initial concerns that the vaccine Ags (iFt or Prevnar®13), if combined during the pulse phase, may compromise the immunostimulatory capacity of the other, PBMCs were pulsed individually with iFt or Prevnar®13, and subsequently combined the iFt and Prevnar 13-pulsed PBMCs just prior to immunization. Following Ft or Sp challenge of mice immunized with either the individual or combined PBMC-based vaccines, we observed that approximately 60-75% of mice immunized with either iFt or iFt plus Prevnar®13-pulsed PBMCs survived Ft LVS challenge. Survival of Sp-challenged mice immunized with either Prevnar®13 or iFt plus Prevnar®13-pulsed PBMCs was 85-100%, with no survival being observed in mice immunized with PBS or PBMCs alone (FIGS. 6A and 6B). Furthermore, no significant difference in protection was observed when comparing the effectiveness of the single versus combined vaccines. These studies were then repeated with iFt and Prevnar®13 being combined during the pulse phase (FIGS. 5C and D). Results were similar to those in or Sp-specific Abs. In regard to the central focus on the generation of humoral (Ab) responses, evidence indicates that Ab is key to protection against Sp. In addition, Ab can also play a key role in protection against Ft LVS. Nevertheless, cellular immunity can also play a significant role in the latter.

Figure 7:
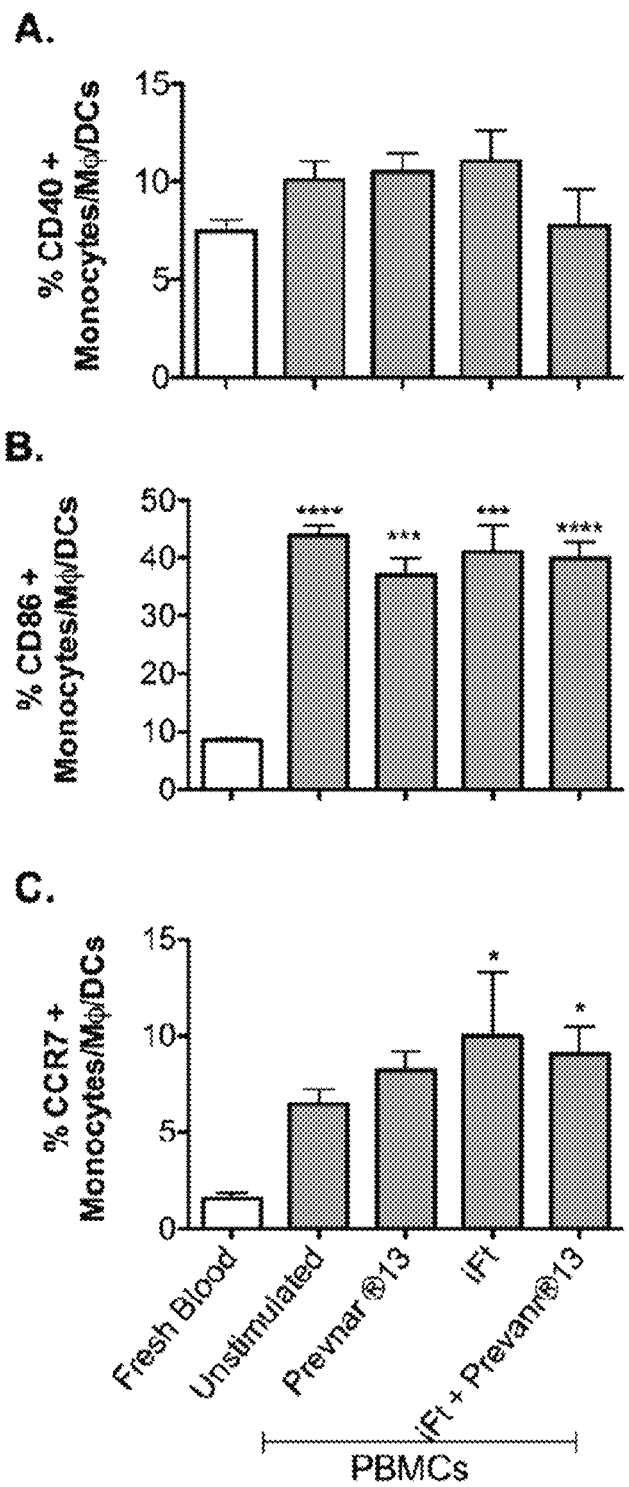

The precise mechanism(s) by which Ag-pulsed PBMC's induce protective immunity remains to be determined. However, it is worth noting that APCs within the PBMC population not only include DCs, but also monocytes/macrophages and B cells, all of which could synergize to produce a more diverse and potent immune response. Furthermore, analysis of PBMCs for activation markers pre and post-PBMC isolation indicate that cellular activation within the PBMC population following density gradient separation does occur, as seen in FIG. 7. The results in FIG. 7 were obtained from freshly isolated PBMCs that either remained unstimulated or were pulsed with iFt, Prevnar®13, or both, as described above. After pulsing, PBMCs were stained for expression of activation markers with the following monoclonal antibodies: anti-CD11b-Alexa fluor 488, anti-CD19-PE, anti-CD40-APC, anti-CD86-Alexa fluor 700, or anti-CD197-PE-Cy7 BD (Biosciences, San Jose, Calif.). Also, freshly isolated blood was similarly stained to evaluate baseline expression levels of the above activation markers prior to density gradient separation. PBMCs were then analyzed by flow cytometry. Importantly, activated APCs within the PBMC population would be better equipped to stimulate an immune response in terms of processing and presenting Ags, secreting pro-inflammatory cytokines, and migrating to lymphoid tissues, once introduced into host tissues. During the Ag-pulsing of PBMCs, APCs may also be activated by adjuvants such as that contained in Prevnar®13, through the engagement of Pathogen Associated Molecular Pattern molecules (PAMPs) found on iFt, and/or cellular debris resulting from the in vitro isolation/processing of PBMCs. Thus, such activation likely does contribute to a positive impact on the downstream immune response generated by Ag-pulsed PBMCs. In addition, the experimental parameters utilized in this study, such as the PBMC isolation method, medium used during pulsing, use of APC activation factors, time of incubation, number of PBMCs, Ag dose, ratio of Ag to PBMC, and the method of administration of Ag-pulsed PBMCs may impact the potency and efficacy of this approach. Thus, further optimization will be required, in particular when applied to humans.

While different routes of immunization may be preferable dependent on the pathogen and immune mechanisms(s) required for protection, the i.n. route induced better protection against Sp compared to the i.v route. Conversely, the i.v. route evoked a more favorable immune response in the case of Ft. Importantly, the i.n. route offers numerous advantages including ease of administration and the ability to induce strong mucosal and parenteral immune responses. The differences based on vaccination route that were observed may be due to a number of factors such as inherent differences in vaccine Ags (Prevnar 13, which is a protein-carbohydrate conjugate vaccine versus iFt, a whole cell inactivated vaccine). Also, recent studies have noted the role of addressing in adhesion of naive lymphocytes to high endothelial venules at mucosal sites. In the case of Ag-pulsed PBMCs, the pulsed immunocytes might more easily gain direct access to lymphoid tissues through such mechanisms, as compared to the i.v. route. Alternatively, differential immune requirements of the respective pathogens for immune protection could also explain this difference. In addition to the above, there are a multitude of additional factors that may also explain this observation. First, the polysaccharide Ags in Prevnar®13 versus the whole cell Ags of iFt may have distinct pharmacokinetics. Second, Ft is known to induce distinct immune responses depending on the route of introduction. Specifically, when utilizing the i.n. route, an IL-17 dominant response is produced, whereas a response favoring IFN-γ production is produced via the dermal route. Also, the i.v. route has been found to be less effective at inducing an immune response to Ag (peptide)-pulsed DC vaccines as compared to s.c., i.p. and i.d. routes. Thus, it is possible that polysaccharide conjugate vaccines such as Prevnar®13 follow a similar pattern. If so, Prevnar® 13-pulsed PBMCs may produce considerably lower immune responses by the i.v. route as compared to the i.n. route. Never the less, studies in this regard are very limited and further study will be needed to determine the optimal immunization route based on the specific pathogen for which the vaccine is being developed.

The observation that protective immune responses to two different vaccine Ags can be achieved when pulsing PBMCs simultaneously with those Ags suggests that this approach might also provide a multi-organism vaccine platform. If confirmed in humans, this vaccine strategy could significantly reduce the costs and trauma of immunization by a) reducing vaccine dose magnitude; b) reducing vaccination clinic visits needed to achieve protection against multiple diseases; and c) reducing the number of injections required for currently recommended immunizations. Importantly, while the studies presented suggest this to be a very promising approach to multivalent vaccination, as well as vaccination in general, further research is needed to determine the maximal number of vaccine Ags, which can induce protective responses after simultaneous PBMC pulsing, the lowest doses of Ags and shortest pulse periods required, and the relationship of the findings in mice to those in human subjects. It is also important to note that the pooling of blood from multiple donors required to conduct mouse studies would not be necessary in the case of humans, since the pulsed PBMCs will be isogenic (either obtained from the recipients blood or cord blood) in which case MLR reactions would not be a concern. Also, we do not know the number of PBMCs that will be required for translation of this strategy to Humans. This will require clinical studies. However, in one DC-based immunotherapy study approximately $50 \times 10^6$ Ag-pulsed DCs were delivered into a human donor. To obtain $50 \times 10^6$ PBMCs approximately 10-15 ml blood would be required, which is easily achieved. For immunoprophylaxis lower amounts could be used.

Demonstration of polyvalent simultaneous immunization using the i.n. route also provides a basis for studies to determine whether this method/route can be made practical for field use by further simplification (elimination of wash steps, separation of PBMC's by simple centrifugation, possible use of cord blood, etc.). Other applications could include: multiple simultaneous immunizations against bioterrorism agents, testing of adjuvants, reducing adjuvant toxicity, and evaluation of potential utility with DNA vaccines, as well as prophylactic or therapeutic immunization against diseases for which currently available vaccines are either suboptimal or nonexistent.

A new method of vaccination based on ex vivo Ag pulsing of PBMCs has thus been shown to protect mice from lethal challenge with Ft and Sp. In regard to the latter, administration of Ag-pulsed PBMC's induced more marked, stronger, and longer-lived Sp specific Ab responses and enhanced survival. Furthermore, potential for the use of this strategy as a multi-organism/multivalent vaccine platform was demonstrated. If adaptable for human use, this new method could potentially reduce the number of injections, clinic visits, and costs needed to provide protection against vaccine preventable or vaccine treatable diseases by making possible multiple simultaneous vaccinations in a single clinic visit, as seen in Table 2 below.

TABLE 2

Estimated cost reductions resulting from the use of PBMC-based vaccination

|  | Shots | Clinic Visits | Cost Per Infant* | Total Cost (USA)** |
|---|---|---|---|---|
| Current CDC Recommendations | 16*** | 7.5 | $2,255 | $9 billion/year |
| Utilizing PBMC-Based Vaccination | 6 | 3.75 | $1,127 | $4 billion/year |

*Cost comparisons based on data provided in the following references:
1. http://www.cdc.gov/vaccines/parents/downloads/parent-ver-sch-0-6yrs.pdf
2. http://www.cdc.gov/vaccines/hcp/patient-ed/conversations/downloads/fs-combo-vac.pdf
3. http://pediatrics.aappublications.org/content/124/Supplement_5/S492
4. http://medicaleconomics.modernmedicine.com/medical-economics/content/tags/american-academy-pediatrics/immunizations-how-make-vital-service-fina
5. http://www.cdc.gov/vaccines/programs/vfc/awardees/vaccine-management/price-list/
**Represents a birth cohort of 4 million infants/year.
***Would be 32 shots without the use of combination vaccines.

Childhood vaccines required to protect children from disease now number approximately 14 and a child may receive up to 16 vaccine injections between birth and 6 years of age. Administration of these vaccines is not only traumatic for the child and parent, but also involves substantial costs associated with each vaccine preparation, including the costs for development, production, packaging, storage, distribution, and administration of each individual vaccine.

Furthermore, the number of office visits required to administer the full regimen of required immunizations consumes substantial clinical resources, including supplies and man-hours, which may be in short supply in many countries. Additionally, no less than 145 new vaccines are currently in development making the prospect for future vaccination programs problematic. Thus, there is a need for a universal multivalent/multi-organism vaccine platform that efficiently and effectively combines these vaccines into a single immunization regimen. The ability to administer a large number of vaccines in a single bolus using the ex vivo PBMC-based vaccine strategy that we demonstrate in this manuscript would not only substantially reduce the number of vaccine injections required, but also thereby reduce costs as shown above, while also significantly improving compliance and coverage, most notably in third world countries where storage capacity is limited and repeated travel to a clinic may be difficult or impossible. Another potential application is use during bioterrorism attacks when multiple simultaneous immunizations may carry life and death significance.

In addition, while many potent adjuvants are currently available, only aluminum salts are approved for human use in the U.S., due primarily to toxicity and safety concerns regarding other adjuvants. Thus, there is also a need for the identification of powerful and less toxic adjuvants, or a mechanism by which the toxicity of currently available adjuvants can be obviated. To date, research focused on identifying better adjuvants for human use, which can also be FDA approved, has yet to succeed. Pulsing PBMCs ex vivo with vaccine Ag(s) plus adjuvant, followed by their removal prior to re-administration of the pulsed PBMCs, could substantially reduce or eliminate adjuvant toxicity, while also significantly increasing the availability of more potent and broadly stimulatory adjuvants for clinical use. Thus, the PBMC platform can also be used to screen candidate adjuvants with candidate vaccines to select those providing best immunogenicity and protective efficacy in the individual or animal receiving the pulsed PBMCs treated with said vaccines and adjuvants. The PBMC platform can also be used to detect any adverse effects of given adjuvant(s) or vaccines on the PBMCs as evidenced by morphologic changes or interference with immunogenicity or protective efficacy as seen in Table 3 below:

Table 3—Candidate Vaccine Plus Adjuvant Screening Using PBMC Platform

PBMCs pulsed ex-vivo with candidate vaccine plus antigen combination
Washing removes XS vaccine and adjuvant
Pulsed PBMCs given by I.N. (or by other route) to original PBMC donor
Determine humoral, cellular immune and protective efficacy challenge responses Lastly, dendritic cells (DCs) play a central role in generating immunity to infection. Specifically, DCs are highly efficient at taking up, processing, and presenting Ags to naïve T cells. This has led to studies focused on DC-based therapeutics and vaccines against cancer and some infectious diseases, including HIV-1 and influenza. It has also led to the general belief that the use of purified DCs or DCs generated ex vivo, is required for such ex vivo approaches to be effective. However, the generation and/or isolation of DCs ex vivo can require substantial time and expense. The vaccine strategy of the present invention can eliminate the need for purified DCs.

The successful development of the proposed multivalent vaccine platform could have a substantial impact in a number of specific areas: (i) by making possible multiple simultaneous immunizations with a single needle stick to draw the initial blood sample and obtain PBMCs, thereby reducing vaccination needle sticks and reducing significant trauma to children undergoing vaccination; (ii) by reducing vaccination costs via a reduction in the number of required childhood immunizations and required clinic visits; (iii) by increasing patient and parent/guardian compliance and consequently vaccine coverage as a result of decreasing required clinic visits; (iv) by obviating adjuvant toxicity as a consequence of ex vivo adjuvant use prior to administration, thereby increasing the number of potential adjuvants available for human use; (v) by allowing the use of PBMCs in place of DCs, thereby reducing the complexity, time, and costs associated with ex-vivo DC-based vaccines and therapeutics and creating a simplified and less costly regimen with potential application to cancer therapy, as well as infectious disease vaccines.

In summary, the significance of the described studies and vaccine strategy is substantial, in that the successful development of this PBMC-based vaccine platform will address key limitations to current vaccination strategies and fundamentally transform the paradigm for vaccine administration, adjuvant use, and DC-based therapeutics.

For example, the PBMC vaccination platform model of the present invention can be used to screen new candidate vaccine and adjuvant combinations to determine which ones result in the best immunogenicity and protective efficacy in the PBMC model. This approach will facilitate accelerated selection of candidate vaccine and adjuvant combinations for human and veterinary animal use in clinical trials.

In addition, the PBMC vaccination platform model of the present invention can also be used to screen new candidate vaccine and adjuvant combinations to determine which ones have the most favorable safety and toxicity profiles regarding their effects on PBMCs.

The PBMC vaccination platform model of the present invention also permits use of vaccine adjuvant combinations utilizing adjuvants considered unsuitable for in vivo use in human subjects, given that after exposure of PBMCs ex vivo to the vaccine adjuvant combinations, the adjuvants can be removed by washing before administering the pulsed PBMCs back to the recipient.

What is claimed is:

1. A screening platform, comprising an amount of peripheral blood mononuclear cells that have been pulsed ex vivo with at least one vaccine and an adjuvant, wherein the amount of peripheral blood mononuclear cells does not include the vaccine and the adjuvant and wherein the amount of peripheral blood mononuclear cells exhibit an immunogenicity and a morphology that is different than if the amount of peripheral blood mononuclear cells were not pulsed ex vivo with the at least one vaccine and the adjuvant.

2. The system of claim 1, wherein the at least one vaccine comprises a first antigen and a second antigen that is different than the first antigen.

3. The system of claim 2, wherein the first antigen is inactivated *F. tularensis* LVS (iFt) and the second antigen is an *S. pneumoniae* vaccine.

4. The system of claim 1, wherein the adjuvant is unsuitable for in vivo use in humans.

* * * * *